United States Patent
Miller et al.

(12) 
(10) Patent No.: US 6,236,944 B1
(45) Date of Patent: May 22, 2001

(54) EXPERT SYSTEM FOR ANALYSIS OF DNA SEQUENCING ELECTROPHEROGRAMS

(75) Inventors: Arthur W. Miller, Boston; Barry L. Karger, Newton, both of MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 09/291,679

(22) Filed: Apr. 14, 1999

Related U.S. Application Data

(60) Provisional application No. 60/081,990, filed on Apr. 16, 1998.

(51) Int. Cl.[7] ............... G01N 33/48; G01N 33/50; G06F 19/00; C12Q 1/70; C12Q 1/68
(52) U.S. Cl. .................. 702/19; 702/20; 435/6; 435/91.1; 435/287.1
(58) Field of Search .............. 435/6, 91.1, 287.1; 536/23.1; 364/148.07, 497, 413.01, 554, 496; 702/19, 20

(56) References Cited

U.S. PATENT DOCUMENTS

| | | | |
|---|---|---|---|
| 5,119,470 | * | 6/1992 | Highland et al. .............. 395/64 |
| 5,326,692 | * | 7/1994 | Brinkley et al. .............. 435/6 |
| 5,365,455 | * | 11/1994 | Tibbetts et al. .............. 364/497 |
| 5,552,028 | * | 9/1996 | Madabhushi et al. .............. 204/451 |
| 5,582,705 | * | 12/1996 | Yeung et al. .............. 204/603 |
| 5,916,747 | * | 6/1999 | Gilchrist et al. .............. 435/6 |

OTHER PUBLICATIONS

Koutny LB et al, "Expert system for data acquisition to achieve a constant signal–to–noise ratio: application to imaging of DNA sequencing gels", Analytical Chemistry, vol.65, No.2, Jan. 15, 1993, pp. 148–152.*

* cited by examiner

*Primary Examiner*—John S. Brusca
*Assistant Examiner*—Stephen Siu
(74) *Attorney, Agent, or Firm*—Weingarten, Schurgin, Gagnebin & Hayes LLP

(57) ABSTRACT

A method of analyzing DNA fragments separated electrophoretically is presented. The method includes the use of an expert system that interprets raw or preprocessed signal from the separation. The expert system can be used for real-time base-calling, or applied offline after data acquisition is complete. The expert system is directly applicable to all types of electrophoretic separation used for DNA sequencing, i.e. slab gel, capillary and microchip. Each lane of a multiplex system can consist of 1 to 4 (or even more) different fragment labels. The expert system may also be used with other base-coding schemes, such as those in which more than one base is labeled with a given dye, but the amount of label is different for each base. When the presently disclosed method is applied to DNA sequencing, the resulting interpretation comprises a DNA base sequence with numerical confidences assigned to each base. By use of the presently disclosed method the degree of automation of data processing in high-throughput DNA sequencing is improved, as is the quality of the results.

6 Claims, 6 Drawing Sheets

A general rule:

If dye mobility shifts known and peak locations unkown, then determine peak locations based on noise threshold.

A rule for modifying estimated number of bases in a peak (N):

If local average peak resolution <= 0.3 and peak area small for N bases, then subtract 1 from N.

A post-processing rule:

If base-calls are final and base-call confidences have been assigned, then halt inference and output results.

*FIG. 3*

EXPERT SYSTEM FOR ANALYSIS OF DNA SEQUENCING ELECTROPHEROGRAMS

CROSS REFERENCE TO RELATED APPLICATIONS

This application claims the benefit under 35 U.S.C. §119 (e) to provisional patent application Ser. No. 60/081,990 filed Apr. 16, 1998; the disclosure of which is incorporated herein by reference.

STATEMENT REGARDING FEDERALLY SPONSORED RESEARCH OR DEVELOPMENT

Part of the work leading to this invention was made with United States Government funds under Human Genome Project Grant Number DE-FG02-90ER 60985.

BACKGROUND OF THE INVENTION

The volume of data now produced by automated DNA sequencing instruments has made fully automatic data processing necessary. The raw data from these instruments is a signal produced by a sequence of electrophoretically separated DNA fragments labeled with reporter groups, typically but not always with various fluorescent dyes. Data processing entails detecting the fluorescence peaks for each fragment, determining which dyes they correspond to, and constructing a DNA base sequence corresponding to the determined fragments. This overall procedure is known as base-calling. Base-calling software must produce very accurate sequences and supply numerical confidence estimates on the bases, to preclude expensive and time-consuming editing of the resulting sequence by technicians.

Approaches to the base-calling problem include neural networks [Tibbetts et al., 1994; U.S. Pat. Nos. 5,365,455 & 5,502,773], graph theory [Berno, 1996], homomorphic deconvolution [Ives et al., 1994; U.S. Pat. No. 5,273,632], modular ("object oriented") feature detection and evaluation [Giddings et al., 1993 & 1998], classification schemes [Li and Yeung, 1995; WO 96/36872 & others], correlation analysis [Daly, 1996], and Fourier analysis followed by dynamic programming [Ewing et al., 1998]. Additional related patents describe base-calling by blind deconvolution combined with fuzzy logic [Marks, WO 98/11258], by comparison to a calibration set of two-base prototypes in high dimensional "configuration space" [CuraGen, WO 96/35810], and by comparison to singleton peak models [Visible Genetics, WO 98/00708]. There are also several reports specifically related to confidence estimates [Lipshutz et al., 1994; Lawrence and Solovyev, 1994; Ewing and Green, 1998]

The neural network approach (Tibbetts) only functions well when the input data are very similar to the training set. This requires retraining for each type of instrument, dye chemistry, and set of separation conditions. It is difficult or impossible to make small changes to, or to extend for other types of datasets, the output of a particular training session. Furthermore, the types of neural networks whose internal operations in obtaining a particular result can be readily explained are the least capable class of neural network.

The graph-theoretic approach (Berno) relies on effective deconvolution by a crude peak-sharpening filter. This produces a lot of noise peaks, which the method attempts to winnow out based on poor height and spacing. The filter is fast but does not result in a high-quality deconvolution, and the winnowing procedure is inflexible.

The homomorphic deconvolution (Ives) uses blind deconvolution to enhance information on peak location. However, the subsequent peak detection and base assignments are overly simplistic.

An object-oriented method (Giddings) tries to adopt a flexible, modular program design, in which each piece is as independent as possible from the rest of the program. Preprocessing is done in many independent steps by different user-configurable tools. Subsequent base-calling is done by combining independent confidences on quality of peak spacing, peak height, and peak width. Considerable time must be spent by the user to configure the modules for a particular type of data. Moreover, the base-calling module is relatively unsophisticated. More abstractly, some tasks may be intrinsically dependent on each other, creating problems when the tasks are separated into independent modules. The most recent implementation uses deconvolution to increase accuracy, but this greatly increases execution time and can create artifact peaks, and it also requires finely tuned digital filtering.

The classification of channel amplitude ratios at peak positions (Li & Yeung) is restricted to relatively high peak resolution and high signal-to-noise ratios.

The method of Fourier analysis followed by dynamic programming (Ewing) exploits the regularity of peak spacing in properly preprocessed data. Base-calling matches observed peaks to predicted base positions. The method relies heavily on optimized preprocessing (color separation, noise removal, background subtraction, amplitude normalization, and peak repositioning), and poorly predicts base positions at low peak resolution. It is relatively inflexible and difficult to extend or adapt to changes in data characteristics; e.g., data resulting from a new protocol that gives more variable peak spacing.

The fuzzy logic approach (Marks) as described requires prior deconvolution. Furthermore, the inference system is limited in the complexity of the rules that can be incorporated, especially if they must be optimized.

The use of two-base prototypes (CuraGen) suffers from problems similar to the neural network method.

The use of singleton peak models (Visible Genetics) does not provide for complex relations between peaks and base-calls.

An expert system simulates the reasoning of human experts in a particular problem domain. Expert systems are most often useful for applications in which human experts perform well and can describe their reasoning in detail. The expert system consists primarily of a set of if-then rules, sometimes called productions, and a mechanism to reason with them, usually called an inference engine [Stefik, 1995; Durkin, 1994; Jackson, 1990]. The firing of a rule causes an action to be taken; e.g., adding to working memory the knowledge that a particular peak in the fluorescence signal has a certain width or contains a particular number of bases.

The pervasive limitations in prior art for base-calling are the lack of integration among subtasks, and the relative absence of flexibility and sophistication in the methods that assign bases to peaks. The principal benefits of a production system over prior art are in the ability to produce very high integration and complex, sophisticated program logic in a form that is easy for people to understand and extend. This is because the rules can be stated in natural language (e.g., English), and because greater generality, flexibility, and accuracy can be obtained simply by adding new rules or modifying existing ones. The inference engine can then combine the rules to produce a degree of integration, sophistication, and thoroughness that is hard to reproduce by an orthodox procedural software approach.

BRIEF SUMMARY OF THE INVENTION

A method of analyzing DNA fragments separated electrophoretically is presented. The method includes the use of an expert system that interprets raw or preprocessed signal from the separation. The expert system can be used for real-time base-calling, or applied offline after data acquisition is complete. The expert system is directly applicable to all types of electrophoretic separation used for DNA sequencing, i.e. slab gel, capillary and microchip. Each lane of a multiplex system can consist of 1 to 4 (or even more) different fragment labels. The expert system may also be used with other base-coding schemes, such as those in which more than one base is labeled with a given dye, but the amount of label is different for each base [Kheterpal et al., 1998]. When the presently disclosed method is applied to DNA sequencing, the resulting interpretation comprises a DNA base sequence with numerical confidences assigned to each base. By use of the presently disclosed method the degree of automation of data processing in high-throughput DNA sequencing is improved, as is the quality of the results.

BRIEF DESCRIPTION OF THE SEVERAL VIEWS OF THE DRAWING

The invention will be more fully understood from the following detailed description taken in conjunction with the accompanying drawings wherein:

FIG. 3 is a partial listing of some rules utilized in the presently disclosed method;

DETAILED DESCRIPTION OF THE INVENTION

Figure 1:
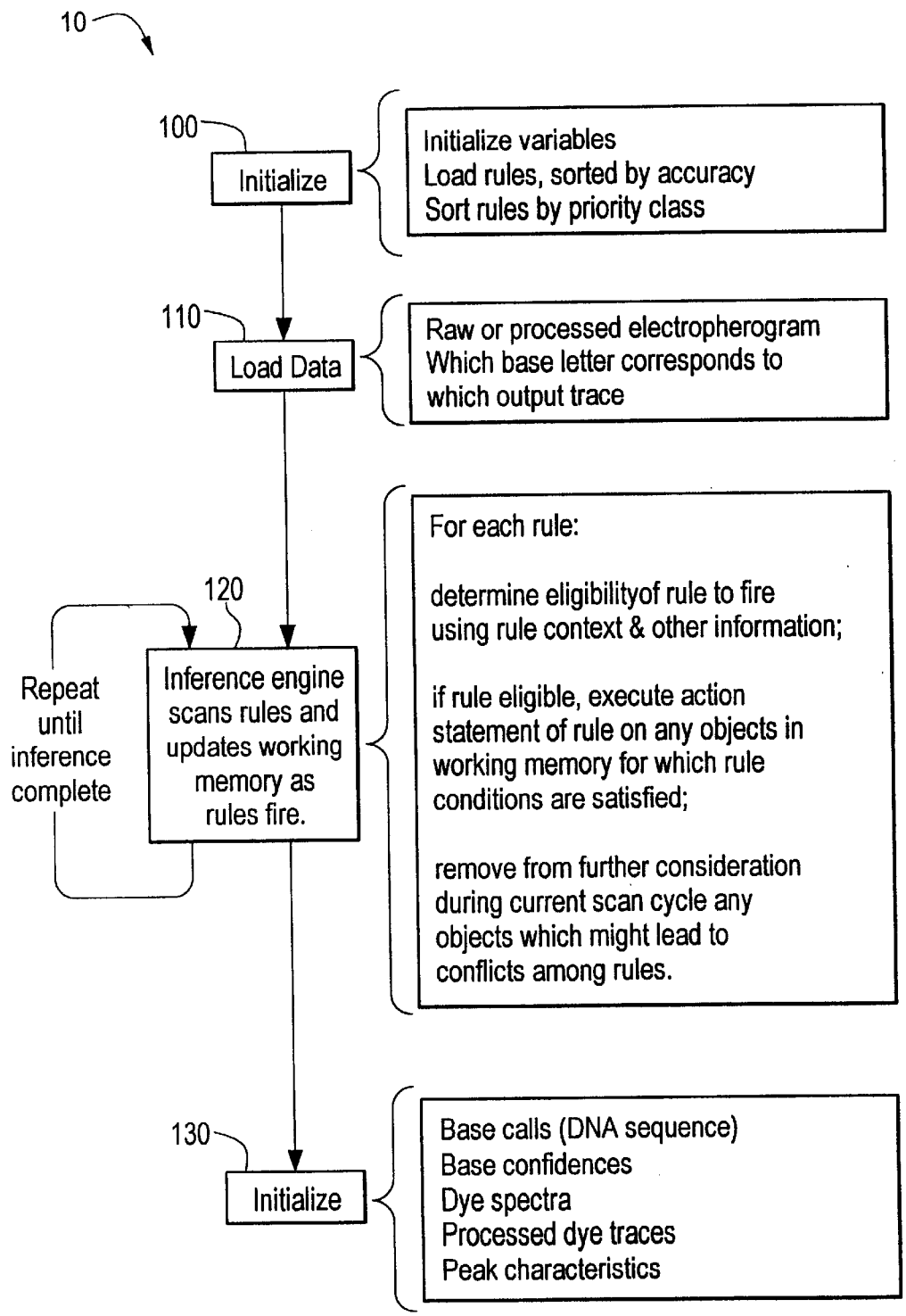
FIG. 1 is a flow chart of the presently disclosed method for analyzing DNA fragments separated electrophoretically.

A method for analysis of DNA sequencing electropherograms includes the use of an expert system. The expert system includes a knowledge base and an inference engine. The expert system may be viewed largely as mechanism to detect peaks, and then interpret each peak as arising from noise, an artifact, a particular series of bases, a primer peak, or any other feature occurring in electropherograms for DNA sequencing. These interpretations result from rules for determining which hypothesis about a peak is supported by the most evidence. The general outline of the preferred embodiment of the expert system is shown in FIG. 1 and described later in depth.

Figure 2A:
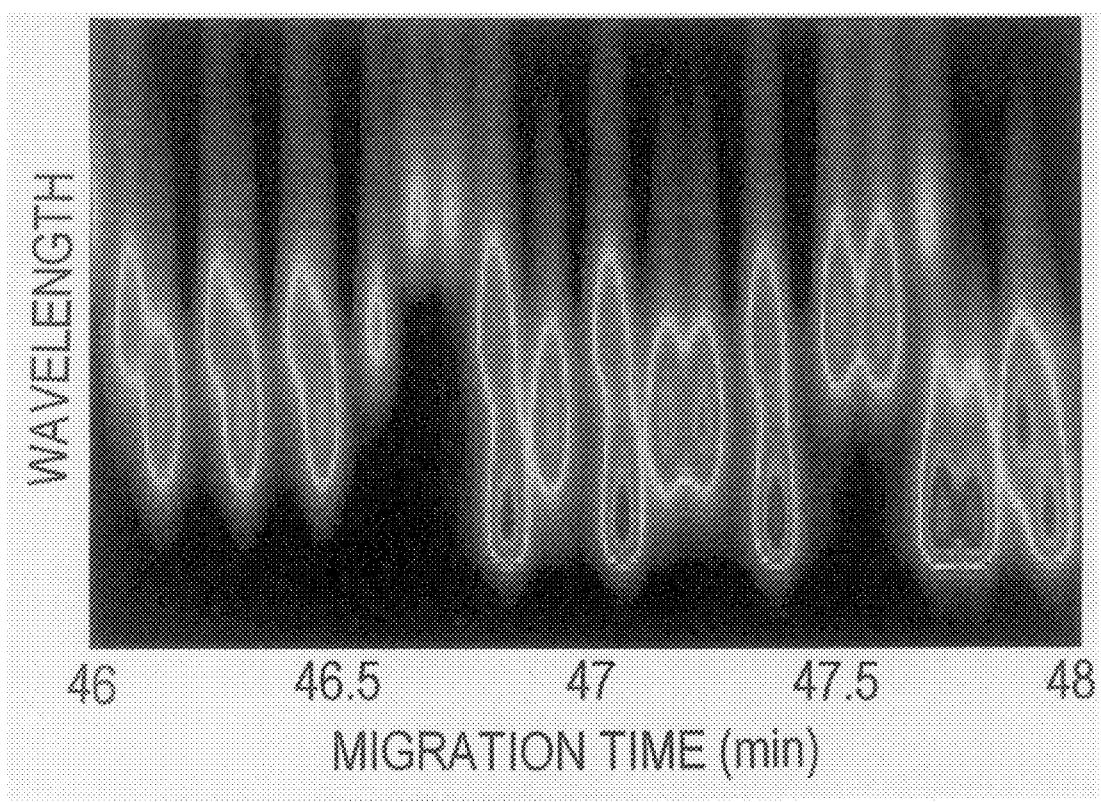
FIG. 2A is a portion of a raw fluorescence signal of an electropherogram.
Figure 2B:
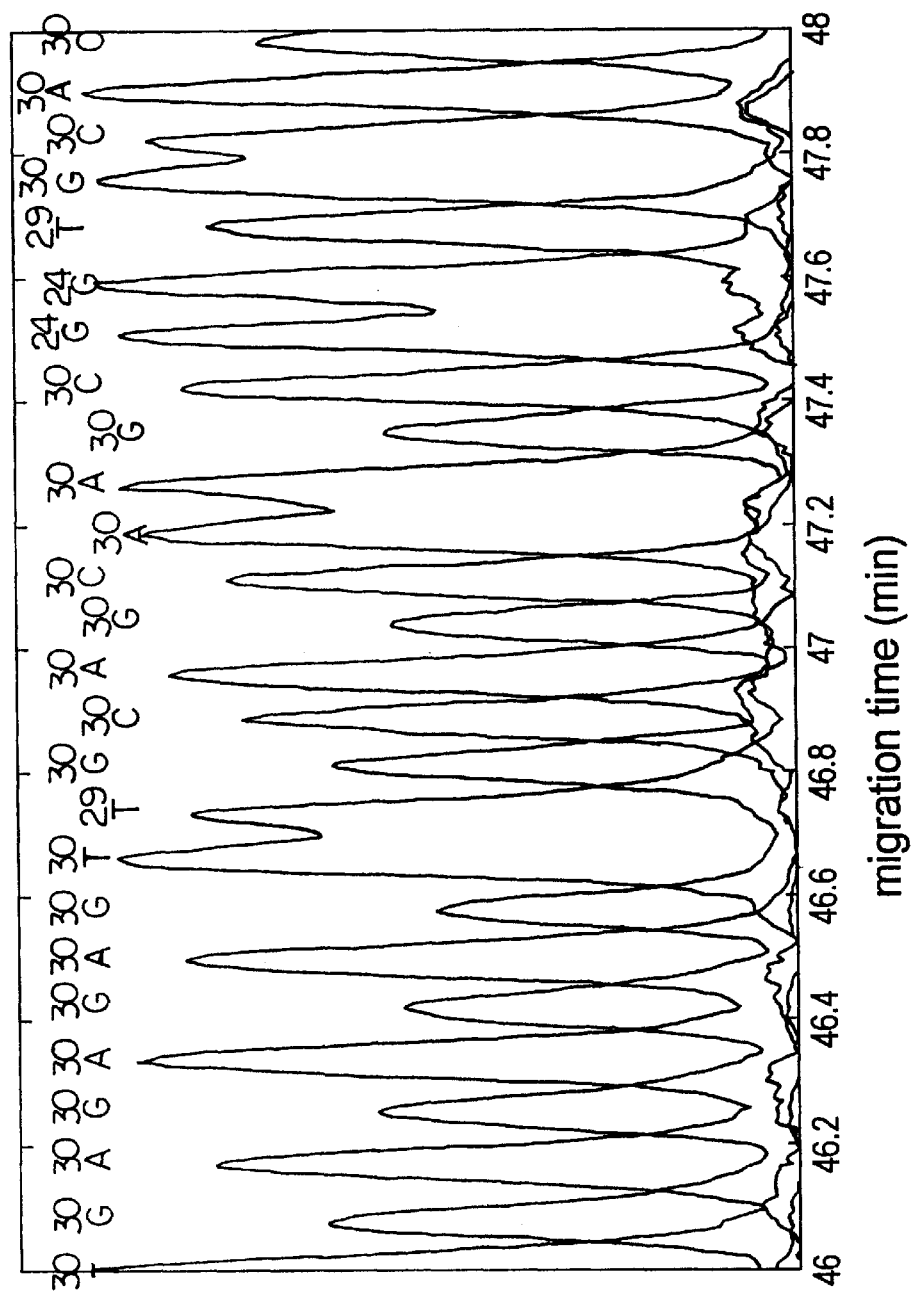
FIG. 2B is a portion of resulting base-calls and associated numerical confidence and processed dye traces.

After initialization and loading of data, a list of rules is scanned repeatedly until inference is complete, and then the results are output. Sample input and the corresponding results are shown in FIG. 2. FIG. 2A shows a short section of full spectral fluorescence data from an electropherogram, with migration time on one axis, spectral wavelength on another, and fluorescent intensity indicated by shading. FIG. 2B shows the principal results inferred from this data: processed dye traces, base-calls, and numerical confidences.

FIG. 3 shows some examples of rules that may be used in proceeding from FIG. 2A to FIG. 2B.

Figure 4:
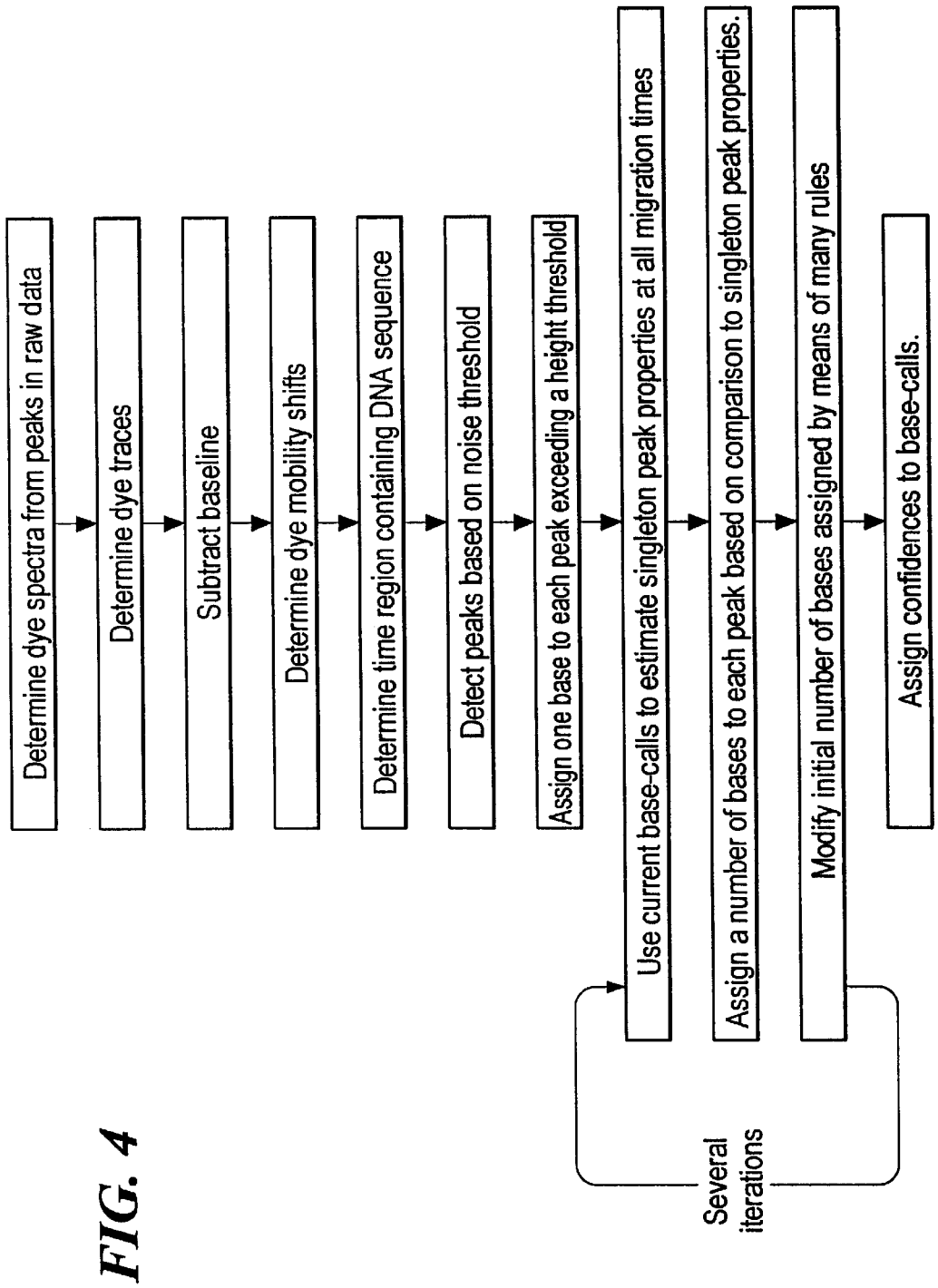
FIG. 4 shows the order of the data processing steps conducted by the expert system.

Typical steps of data processing performed by the base-calling expert system are shown in FIG. 4. The order of steps shown in FIG. 4 is only one of many possible orders, and the steps may be highly intermingled. For example, in real time use, the rules may be designed to perform a cycle in which new fluorescent data arrives, peaks in the new data are detected, the properties of new peaks are measured, and implications of the new peaks are pursued. Such implications would include inferences of the number of bases in the new peaks, updates to migration time-dependent property maps, and examination of nearby peaks to see if their assigned base-calls should be changed based on the new information. Other variations on FIG. 4 include making the first base-calls some distance into the DNA sequence, and subsequent calls towards both earlier and later migration times. The advantage of this alternative is that the initial parameters of peak spacing, dye mobility shifts, etc., are determined in the region where they are most easily obtained. These parameters can then be used to guide base-calling and further parameter determinations elsewhere.

The first step presented in FIG. 4 is determination of the dye spectra. If raw fluorescence data is supplied without known dye spectra, the dye spectra must be determined from the data in order to perform color separation. Color separation is the decorrelation of the raw fluorescence signal into the components produced by individual dyes, each dye representing one "color". In base-calling literature, this has also been called spectral separation, spectral deconvolution, and multicomponent analysis. In one embodiment, the dye spectra are determined by first identifying a short region beginning at the approximate start of the DNA sequence, commonly just after the so-called primer peak. After a rough background subtraction, an initial estimate is calculated of peak positions and which dyes produced them. This estimate is accomplished by clustering the background-corrected spectra from the centers of the most intense peaks. After this, a rough peak shape estimate for the region is determined and a "target" is constructed, this being an approximation of the dye traces (fluorescence signal after color separation) the peaks should produce. The data are then fitted to the target to produce refined estimates of the dye spectra, which are further refined iteratively by analyzing residuals. Because the entire peak shape is used in determined the dye spectra, color separation can be accomplished even if there are no well-resolved peaks in the dataset. While the raw data most commonly comprises four spectral channels, the procedure is identical if more channels are used, and with minor modifications the procedure can be used for fewer than four channels.

Once dye spectra are known, color separation is normally accomplished by least squares estimation (fitting the raw data matrix to the dye spectra). Baseline determination for the resulting dye traces can be done by linearly interpolating between baseline points determined as the minimum amplitude values in time windows on the data. Other order statistics than the minimum may also be used; e.g., the fifth percentile of amplitude values in the window for the channel.

To determine a correct DNA sequence, dye mobility shifts must be determined. These are dye-specific differences in electrophoretic mobility that must be obtained either by calibration or estimated as part of base-calling, unless the electrophoretic data supplied to the base-caller has been preprocessed to correct for these shifts. Failing to correct for mobility shifts could cause bases to be called in reverse order or to be skipped entirely; e.g., only one call would normally be made for two superimposed peaks of different dyes. Several algorithms for determining mobility shifts have been described, which typically conduct local searches in windowed time regions for the set of shifts that result in minimizing some measure of peak overlap between dye channels.

Peaks may be detected by finding regions that exceed a noise threshold, or by other criteria such as local maxima or thresholds for regionally normalized height. Noise may be estimated as the difference between the channel amplitude before and after smoothing, or by some other method. The process of peak detection is intended to identify the smallest regions that the expert system can evaluate separately. Therefore, the initially determined peak may at later stages be split into two or more peaks if it contains sufficiently deep valleys, or if it overlaps in migration time both sides of a sizable peak in another channel, or if other considerations are met.

In the preferred embodiment, each detected peak exceeding a threshold for normalized amplitude is assigned one base, and the initial estimate for each peak (zero or one) is refined by several iterations which begin by using the current base-calls to estimate for any migration time the properties a peak containing exactly one base would hypothetically have if it appeared at that time (height, width, spacing from other peaks, etc.). Actual peak properties are compared to these abstract "singleton peak" values to produce an estimate for the number of base-calls they contain, and rules are subsequently applied to modify this initial number. Additional information that may be maintained is a complete description of the distribution of observed peak heights and spacings, which may be used in later confidence assignment and in automatic determination of the dye chemistry employed to produce the raw data. Knowledge of the dye chemistry may be used to activate different sets of rules optimized for the different chemistries. Alternatively, this knowledge may be supplied along with the electrophoretic data so that it does not need to be inferred.

Probabilistic confidences on base-calls have become important in sequence assembly. In one embodiment, after the final assignment of bases to peaks is achieved, one or more confidences is assigned to each base-call based on a statistical analysis of errors made by the base-caller on electropherograms of known samples. Alternatively, confidence information can be determined concurrently with the base-calls, and even used in deciding the base-calls. A single confidence value can be determined (overall probability of error), or multiple confidence values can be determined which represent probabilities for different eventualities (probability that an 'A' is actually a 'C' or a 'G', etc.). For compatibility with a widely used standard [Ewing & Green, 1998], confidence values are commonly scaled logarithmically:

Confidence value=−10×$\log_{10}$(estimated error probability)

Figure 5:
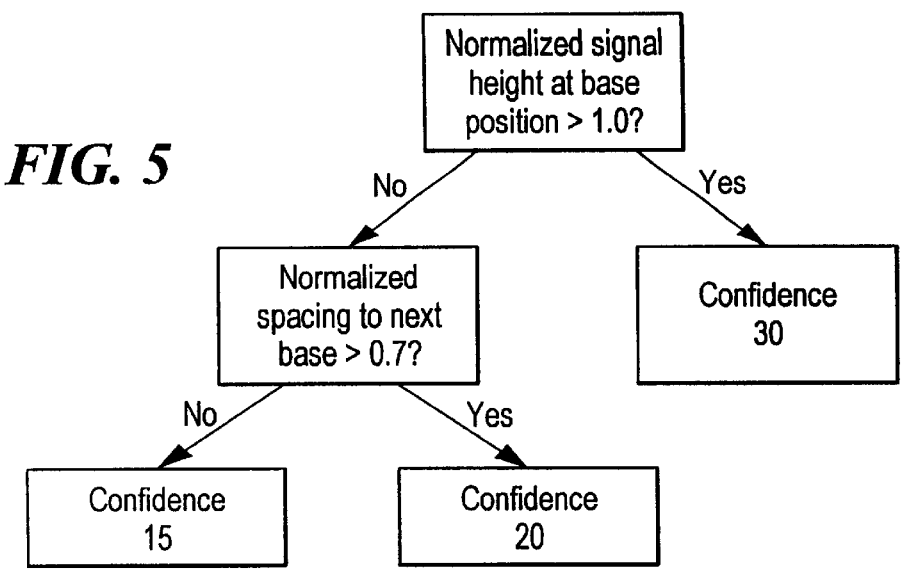
FIG. 5 is a sample decision tree for assigning base confidences.

In a preferred embodiment, confidence values are assigned by decision trees, which classify base-calls by applying a test at each branch. The method used to construct these trees permits a large number of base-call characteristics to be used and does not make restrictive assumptions such as multivariate normality. A simplified decision tree for assigning confidences to called bases is shown in FIG. 5. Decision trees can be determined automatically from a training set by the statistical property information gain, which determines the tests that most accurately classify the instances in the set [Mitchell, 1997]. Because the tree is determined one branch at a time, the paths from top to bottom can be of different length and contain different tests. After determining the tree, confidence values for each leaf (bottom nodes of the tree) are computed from the fraction of correct base-calls in the training set assigned to the leaf.

Figure 6:
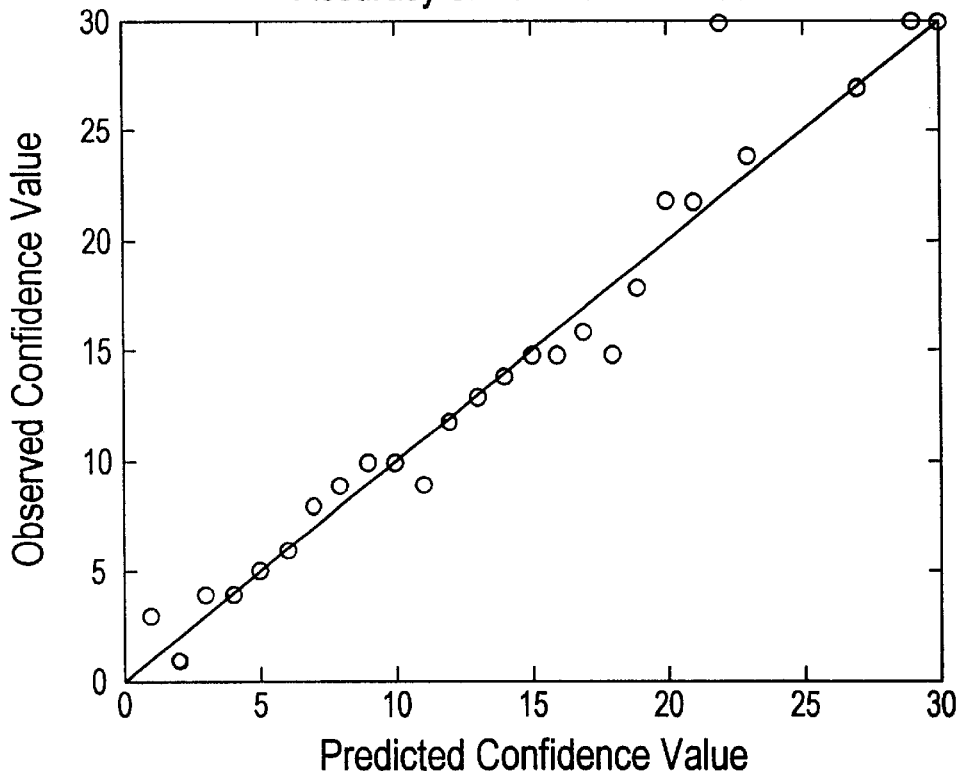
FIG. 6 is a graph of statistical accuracy of assigned base confidences.

FIG. 6 shows the predictive value of confidences determined this way. For a training set of 148 CE electropherograms of varied read length and quality, and run under different conditions of field strength, temperature, and other parameters, base-calling errors were determined by computing a local alignment between the called and known sequences. The resulting 138,000 base-calls contained 2% errors. For each base-call, a common set of features was determined, including peak height, spacing to the next base, and several similar properties. A decision tree was created from the resulting training set and pruned by cross-validation. Accuracy for high confidences was improved by pooling the high-confidence leaves and creating a second tree. Due to the small size of the training set, confidence values greater than 30 were not estimated. FIG. 6 shows the accuracy of the confidences assigned by these trees on a test set of 31,000 base-calls taken from 37 electropherograms not in the training group.

In a particular embodiment, an expert system comprises a minimum of two components, a knowledge base and an inference engine. The knowledge base comprises facts and rules. Facts comprise a raw electropherogram or any other data input, and of anything inferred from this input by the expert system. Such inferred facts may include peak widths, base assignments, base confidences, dye spectra, processed dye traces, or anything else not explicitly stated in the initial rules. In the preferred embodiment rules have the form "if certain conditions are met, then take certain actions (or draw certain conclusions)". It is also possible to have "else" clauses in the rule. The rules can be embedded in the program, executed from a database, or read from a file. An inference engine is a general mechanism to infer new facts from data using the rules. An inference engine can use meta-rules (rules about rules) to guide the reasoning process; e.g. to resolve conflicts among ordinary rules.

Outline of Base-caller

Steps performed by the base-caller include determining the dye spectra from the relatively intense peaks in the raw data, performing color separation via a least-squares fit to these spectra, subtracting baseline, determining dye mobility shifts, detecting peaks based on a noise threshold, and assigning one initial base to each peak exceeding a height threshold. Steps performed subsequently include several iterations in which (1) the expected height and width of peaks containing a single base are estimated for all migration times, (2) an initial number of bases is assigned to each peak based on comparison of the peak's characteristics to those expected for these singleton peaks, and (3) rules are used to modify the initial base estimates. Once base-calls are final, probabilistic confidences are assigned to the base-calls using decision trees.

Referring back to FIG. 1, the start-to-finish operation 10 of the base-caller consists of initialization 100, loading the electrophoretic data 110, repeating the inference cycle (scanning of all rules) until base-calling is complete 120, and outputting the inferred results 130, which include but are not limited to the base-calls and corresponding numerical confidences.

During initialization step 100 counters are initialized, data variables are initialed to "empty", and the rules are loaded and sorted according to meta-rules described later. Each rule is defined by strings that specify a context, a condition and an action. The context string is simply a tag, the use of which is given later in discussion of ordinary rules and meta-rules. The condition and action strings, however, must be converted to executable form, which can be function calls or can be strings to be evaluated by a command interpreter. This conversion can be done, for example, using a string substitution table. Next, at step 110 raw or processed electrophoretic data is read from a file, or is obtained in real-time. The correspondence between bases A, C, G, and T to the output dye traces is specified.

At step 120 the list of rules is scanned one at a time by the inference engine. For each rule, meta-rules determine whether a rule should be permitted to fire. For such rules, the condition statement is evaluated for its truth value. If the condition is true, the action statement is executed. This scanning process is repeated until no rule fires, or a rule fires indicating that the inference is complete, or a nonrecoverable error occurs.

At step 130 the results are output. For each called base, the migration time of the call is corrected for dye mobility shift. Base-calls and other call properties (amplitude, confidence) are sorted in order of increasing value of the corrected migration time. The base-calls and call properties are output. Other items may also be output, including the inferred dye spectra and processed dye traces.

Ordinary Rules and Meta-rules

Rules can be ordinary rules or meta-rules. Meta-rules are general principles to direct the reasoning of the inference engine; e.g., rules about what ordinary rule to apply next, or about how to resolve conflicts. Conflicts occur when the condition statements of two rules are satisfied during a given inference cycle, especially when the corresponding action statements are contradictory. In the preferred embodiment, more than one rule can fire in a given cycle, and rule order and conflict resolution are handled by rule context and rule accuracy. Other conflict-resolution strategies than the one detailed here include use of time tags, rule priorities, or most specific rule first.

The ordinary rules in the preferred embodiment are all used for forward chaining. This means that the program reasons forward from facts to conclusions. However, backward chaining may be added, which assumes a conclusion and searches for facts to support it. In addition, one or more mechanisms could be employed to handle uncertainty. For example, it would be possible to merge fuzzy logic into the system for this purpose. In evaluating a fuzzy version of the statement "peak is small", every peak is determined to be "small" to some degree, but large peaks possess little of this attribute. By avoiding sharp thresholds, fuzzy logic reduces the number of rules required. Additional methods of managing uncertainty that might be employed are certainty factors and probabilities.

A rule might employ a decision tree. For example, a decision tree could be induced for determining base-call estimates from peak features. Then a rule using the tree might state, "if local average resolution is <=0.3, and the number of base-calls currently estimated differs from the number the decision tree provides, then replace the current estimate with the estimate from the decision tree".

In the preferred embodiment, each ordinary rule has an explicitly provided context and an implicit accuracy. The contexts are "general", "assigning bases", and "post-processing", which must be stated when a rule is defined. Before the first inference cycle begins, rules are sorted by decreasing priority of their context, so that all "post-processing" rules (highest priority) precede all "general" rules, which in turn precede all "assigning bases" rules (lowest priority). Within each context, the rules must be presorted so that a more accurate rule always precedes a less accurate rule. It is not a limitation of the invention that rule priority or accuracy must be decided this way; these characteristics might instead be specified explicitly.

Rules may be determined by manual inspection of data, by interviewing experts in the problem domain, or by other knowledge acquisition techniques. Alternatively, various machine learning methods may be applied to determine the rules, and optionally to determine rule confidence or accuracy. Rules may specify measures of uncertainty, as described above, which may be propagated to provide an overall confidence measure for each conclusion. Furthermore, the rules applied to reach a particular conclusion may be recorded so that the reasoning used to reach it may be explained to the user in text form. This is a facility usually provided by expert systems.

The context property of a rule is used as follows. During inference, each time a rule is scanned, its context is compared to the active context. If the rule's context is the same as the active context, the condition statement of the rule is evaluated. If the rule's context is different than the active context, an attempt is made to change the active context to the rule's context, and the rule's condition statement is evaluated only if the attempt is successful. In the preferred embodiment, the attempt to change the active context is always successful if the rule context is not "assigning bases". If the rule context is "assigning bases", it is determined whether there exist detected peaks to assign bases to. If so, the active context is given the value "assigning bases", and each peak is flagged as an active object for inference. If not, the context is set to the empty context, and any objects flagged as active are reflagged as inactive.

When the context is "assigning bases", each corresponding rule is tested for all active objects. If the rule condition is met, the action statement is executed for the object, and the object is flagged as inactive. The result of this procedure is that at most one rule fires for each active object, preventing rule conflicts and minimizing the number of rules tested. The first rule to fire for an object will always be the most accurate rule.

It is a feature of these meta-rules that efficiency is made high by preventing an excessive number of rules from being evaluated in each inference cycle, and by minimizing the computational overhead of conflict resolution.

Maps of Migration-time Dependent Properties

Many of the rules require comparing a peak against a prototype "singleton" peak, a hypothetical peak corresponding to precisely one base. Because peak height, width, and other properties are different depending on dye channel and migration time, property "maps" are constructed that allow singleton peak properties to be estimated for any dye channel and migration time. Each map consists of a set of records, each record consisting of a migration time and one or more property values for that migration time; e.g., migration time plus the expected singleton peak height for each dye channel at that time. The records are sorted in order of increasing migration time for efficient look up by binary search. Given a map and a migration time to look up the property value for, if the time is less than the time given in the first record in the map, the property value from the first record is used. If the time is greater than the time in the last record, the property value from the last record is used. For all other cases, the desired property value is interpolated to the desired migration time from the records in the map.

Construction of property maps may be informed by prior knowledge about a property. For example, base spacing is commonly observed to approximate a quadratic function of migration time. Therefore the data in the spacing map may be replaced by or extrapolated from a fit of the measured values to such a function. Furthermore, lookups have no need to be done by simple linear interpolation; various forms of smoothing and modeling can be applied, to even out irregularities in the map; e.g., cubic splines.

Migration-time dependent properties other than those of singleton peaks are given similar maps. These properties include noise level and dye mobility shifts. The data structures used to represent maps may be tables, matrices, ANSI C++ Standard Template Library (STL) map containers, linked lists, or other structure types. The STL map representation, based on red-black trees, can be updated extremely efficiently, lending itself to real-time or other very fine-grained usage. For example, each time a peak is assigned bases, or the assignment is modified, the maps can be updated to immediately reflect the new state.

A Set of Base-calling Rules

The quantity 'N' referred to in the rules is an integer number of base-calls to assign in a rule being applied to a peak object.

Rule 1:
  Context=general
  Condition=dye spectra unknown
  Action=determine dye spectra
Rule 2:
  Context=general
  Condition=dye spectra known and dye traces unknown
  Action=determine dye traces
Rule 3:
  Context=general
  Condition=dye traces known and peak-containing region unknown
  Action=determine peak-containing region
Rule 4:
  Context=general
  Condition=peak-containing region known and dye mobility shifts unknown
  Action=determine dye mobility shifts
Rule 5:
  Context=general
  Condition=dye mobility shifts known and individual peak locations unknown
  Action=determine individual peak locations
Rule 6:
  Context=general
  Condition=individual peak locations known and no base-calls exist
  Action=make initial base-calls
Rule 7:
  Context=general
  Condition=base-calls exist
  Action=estimate singleton peak properties
Rule 8:
  Context=general
  Condition=singleton peak widths are accurate and signal derivatives undetermined
  Action=determine signal derivatives
Rule 9:
  Context=general
  Condition=signal derivatives determined
  Action=subdivide peaks using derivatives
Rule 10:
  Context=general
  Condition=base-calls exist
  Action=measure properties of all peaks, use to estimate number of base-calls (N)
Rule 11:
  Context=assigning bases
  Condition=peak area not positive
  Action=set N to zero
Rule 12:
  Context=assigning bases
  Condition=local average resolution <0.8 and normalized peak skyline <0.2 and normalized peak height <0.5
  Action=set N to zero
Rule 13:
  Context=assigning bases
  Condition=local average resolution >=0.8 and normalized peak height <0.5
  Action=set N to zero
Rule 14:
  Context=assigning bases
  Condition=N is zero and peak area & height exceed thresholds for one base
  Action=set N to 1
Rule 15:
  Context=assigning bases
  Condition=local average resolution >=0.5 and N=$N_{min}$ (defined later) and normalized peak height >1.3 and peak is unusually wide for only N bases
  Action=add 1 to N
Rule 16:
  Context=assigning bases
  Condition=local average resolution <=0.3 and peak area small for N bases
  Action=subtract 1 from N
Rule 17:
  Context=assigning bases
  Condition=N>0 and number of strong minima in signal second derivative >N
  Action=set N to number of strong minima in signal second derivative
Rule 18:
  Context=assigning bases
  Condition=no other rule for assigning bases has fired
  Action=accept N as correct number of bases
Rule 19:
  Context=post-processing
  Condition=base-calls final and confidences unknown
  Action=determine call positions, call amplitudes, and call confidences
Rule 20:
  Context=post-processing
  Condition=base-calls final and call confidences known
  Action=halt inference Implementation of Rule Statements Statements are listed alphabetically. Implementations are generally given for the positive expression of a statement rather than for the negative one; e.g., "confidences known" is listed, while "confidences unknown" is implied by the obvious logical negation.

Base-calls exist. TRUE if and only if variable PKS.BASES is not empty.

Base-calls final. TRUE if and only if PKS.BASES has been updated at least twice after the second derivative of the dye traces have been determined. Finality could also be determined by convergence (lack of significant change) of the number of base-calls (or some other property) over several iterations of estimation, or by determining that base-call certainty factors or confidences have reached a high enough level.

Confidences known. TRUE if and only if variable PKS.CONFS is not empty.

Determine call amplitudes. For a peak to which a positive number of bases, N, has been assigned, compute an average call amplitude. Do this by assuming that each call corresponds to a peak containing 1/N of the total peak area, and has a Gaussian shape whose width can be obtained from the singleton-peak width map. For each of the N calls, determine a final call amplitude that is the lesser of this average call amplitude and the amplitude observed at the call's determined position. Peak shape in this method could be arbitrary, not just Gaussian. The fundamental underlying peak shape for a local time region can be dynamically estimated given the base-calls; or, any arbitrary shape such as Lorentzian or Voigt (a combination of Lorentzian and Gaussian) can be used. Given any peak shape, the amplitudes could in principle be determined by any of a variety of methods of nonlinear least-squares estimation. This would permit call position to be jointly determined along with call amplitude.

Determine call confidences. Probabilistic confidences on base-calls are determined by traversing decision trees. A decision tree is a set of questions organized in a branching fashion that leads to a classification decision. Starting with a first question about a particular base-call, e.g., "is normalized peak height >0.5?", yes and no answers lead to two or more alternative second questions. When no questions remain along a particular sequence of branches, a classification is assigned; e.g., "confidence that base-call are correct is 98.7%". To construct the decision trees for base-call confidence determination, a training set of electropherograms is selected containing members with varied read length and quality, and run under different conditions of field strength, temperature, and other parameters. For each of these electropherograms, base-calling errors are determined by computing a local alignment between called and known sequences by a Smith-Waterman algorithm. For each base-call, a common set of features is determined, including peak height, spacing to the next base, and several other properties. A decision tree to classify base-calls into correct calls and errors is determined from this information using a variant of the ID3 algorithm.

Variations of the ID3 algorithm may include use of an MDL (minimum description length) principle to minimize the need for post-pruning; use of continuous rather than discrete-valued attributes; and nodes containing tests on multiple properties. Linear discriminant trees and regression trees are also possible. Post-pruning may be done after inducing the tree with a variant the ID3 algorithm; either by use of a validation set, by cross-validation, or by some other method. The training set does not have to contain diverse data, but instead may be split into several different training sets specialized for particular data types. It is not necessary to use a Smith-Waterman method to determine correct base-call classifications (whether a base-call is an error or not) for the training set. Any method that results in primarily correct classification may be used. Note that the training set may contain "noise" (misclassifications), as the ID3 algorithm can be made robust against such noise.

The confidence values are recorded in variable PKS.CONFS.

Determine call positions. For a given peak to which a positive number of bases, N, has been assigned, divide the peak into N regions that each contain fraction 1/N of the total peak area. The position of the ith call is the location marking the area midpoint of the ith region. Other methods include using cues obtained from the second derivative of the signal, or doing full nonlinear least-square modeling using the estimated peak shape. Additional alternative methods include using the minima in the second derivative of the signal, as well as the spacing between these minima. As described above for "determine call amplitudes", nonlinear least squares or other maximum likelihood modeling may also be used, or a simple spacing grid (choosing call position based on position of maximum summed amplitude under a spacing grid with nodes separated by a distance equal to the local estimate of base spacing).

Determine dye mobility shifts. Mobility shifts are determined independently in overlapping time windows by shifting channels relative to each other to find the positions such that high-amplitude sections in any given channel coincides with low-amplitude sections in the others. The results of this procedure are recorded in the variable DYE_SHIFTS, which consists of a map containing migration times and the corresponding shift values for each channel.

Determine dye spectra. A migration time to use is first determined as beginning with the end of the largest-area peak in the electropherogram (the primer peak when using dye primers). The dye spectra are determined using a short time region after this position, typically containing 2000 time points. A rough background subtraction is done for each raw channel, and then the time positions of peak maxima are determined. The spectra at these maxima are weighted by amplitude and statistically clustered into four groups using a K-means algorithm. The four spectra so determined (centroids of the clusters) often represent mixtures of the pure dyes, since under some run conditions employed, even the early base peaks can have significant overlap due to modest resolution and differing mobility shifts. Therefore an additional step is used to refine the clustering results. The preliminary dye spectra are used to make tentative assignments of peaks to dyes. In concert with the average peak shape, these assignments are then employed to construct an estimate of the color-separated dye traces (what the traces should be if the peak assignments were correct). Fitting the raw data to this estimate improves determination the dye spectra by removing the influence of peak overlap. The process is repeated using residual analysis to aid in redetermining base positions.

The dye spectra are recorded in the variable DYE_SPECTRA.

Among methods in which the dye spectra are determined automatically, this method has the advantage that the peaks do not need to be well resolved. This means that faster separations, which have worse resolution, can be analyzed.

Determine dye traces. Color separation is performed by a least-squares fit of the raw data to the dye spectra. The resulting dye traces are divided into sections of 300 time points, and the fifth percentile value among the amplitudes of all data points in each section is computed. This calculation established the background at the center of each section; elsewhere, background is derived by linear interpolation. Background is then subtracted from the initial dye traces.

Methods of color separation include least-squares estimation. If fewer than 4 dyes are present because of an unusual base-coding scheme, a model-selection method may be employed [Kheterpal et al., 1988]. Baseline determination can be done by low-pass filtering, or by various methods from the field of chromatography. It would be possible to adjust previously determined baseline at a later stage by using knowledge of confident base-calls and local peak shape.

The dye traces are recorded in the variable DYE_TRACES.

Determine individual peak locations. First, a table (map) is constructed that can be used to estimate the height of a singleton peak anywhere in the peak-containing region. This table is updated and refined several or many times subsequently. The table is constructed initially by recording in it the maximum amplitude in each channel in each consecutive window of 1000 time points within the peak-containing region.

Next, a similar table is constructed for channel noise. Within the peak-containing region, a noise threshold for peak detection is computed in overlapping 500-point time windows by taking four times the mean square of the difference between the amplitude before and after smoothing with a 5-point Savitzky-Golay filter.

Peaks are determined as any regions exceeding the noise threshold for at least 5 points. A peak is split into multiple peaks if it contains local maxima separated by a dip significantly larger in magnitude than the noise threshold. For each peak region, the precise location of the position of maximum amplitude in the region is determined. Then peak start and end points as the positions of minimum amplitude value between the peak location and the locations of the nearest neighboring peaks to the left and right in the same channel are determined. Peak height is determined as the amplitude at the peak's location.

Locations may be based on a height threshold, or as commonly done in chromatographic software, by use of a slope sensitivity and prior knowledge of minimum peak width. An alternative method for noise determination would be modeling of signal and noise using the power spectrum, which might be determined independently for each dye channel and time region. Noise level might be refined at a later stage by using approximate knowledge of base positions and of the local peak shape to model the true signal, and then subtracting this from the observation to obtain the refined noise estimate.

All information determined for each peak is recorded in the variable PKS.

Determine peak-containing region. The peak-containing region is considered to be the time region containing all peaks corresponding to the DNA base sequence. The start of the peak-containing region is found by creating a vector with an element for each time sample, containing in the ith position the maximum signal among all dye channels at the ith sample. Within this vector, the position, P, of greatest integrated signal over a window of 50 time points is determined. If dye primer chemistry is being used, this will normally locate the so-called primer peak. The beginning of the peak-containing region, B, is a time point located just after the peak with position P. Specifically, B is the largest value among the four time point indexes demarcating the first zero crossing in each channel subsequent to P.

The end of the peak-containing region is determined by locating an increase in the standard deviation of the dye channel amplitude subsequent to position B. The rationale is that the peak region should extend to the end of the data unless a very large peak occurs before the end, which typically marks the emergence of all remaining DNA fragments in an unresolved plug. The specific method for determining the end position first determines a vector that consists of the summed signal for all dyes at each time point. Then overlapping time windows of 500 time points are established on this vector, with the first window beginning at B and the final window not extending beyond the final time point. The standard deviation of the vector values in each window is calculated, and for each window, the minimum standard deviation among all prior windows is noted. The end of the peak-containing region is the start of the window at which the ratio of the window standard deviation to the minimum standard deviation previously observed is at least three, and in which the standard deviation is at least 10% of the standard deviation of the first window. If no such window is detected, the end of the peak-containing region is the final time point.

The beginning of the region might be determined as where peaks exceeding a signal-to-noise threshold were sufficiently numerous and dense to ensure a region containing bases. The endpoints of the region might also be determined dynamically during later stages of base-calling based on areas where average base-call confidence dropped below a threshold, or where peak overlap became high, or where large gaps between peaks occurred.

The starting and ending positions are recorded in the variable PKS_REGION.

Determine signal derivatives. The smoothed second derivative of each dye channel is computed, then the locations of all local minima therein are determined. For the peak-containing region, overlapping windows of 1000 time points are established. The singleton peak width expected in the middle of each window is repeated. For each dye channel, the smoothed second derivative for the window by Savitzky-Golay filtering, using a filter of order M, where M equals (singleton peak width)*square-root(5)/2.355, is computed. The positions and amplitudes of minima in the resulting second derivative signal are then trivially determined. Fourier or wavelet methods could also be utilized. The results are stored in variable Y2.

Dye mobility shifts known. TRUE if and only if variable DYE_SHIFTS is not empty.

Dye spectra known. TRUE if and only if variable DYE_SPECTRA is not empty.

Dye traces known. TRUE if and only if variable DYE_TRACES is not empty.

Estimate singleton peak properties. Use the current set of base-calls to estimate what properties a peak containing exactly one base would have if it occurred at any given migration time; i.e. determine property "maps". This is done by determining the properties at discrete time points, and subsequently interpolating when properties are requested for particular migration times or dye channels. The properties include but may not be restricted to peak height, peak spacing, and full width at half maximum height. Properties are determined at the migration time of each called base using a window about each peak that contains 20 called peaks. Peak spacing is computed as the average spacing of all base-calls in the window. Peak height and width are the average width and height for peaks in the window that currently are assigned exactly one base. If no such peaks are found, width and height are interpolated from surrounding windows. Peak height is determined separately for each channel. For peak spacing, one could find the maximum in the autocorrelation of peak "skyline" (envelope of maximum signal for the amplitude-normalized dye traces, after correcting for mobility shift). We have observed that this works well for peak resolution down to 0.4, as long as signal-to-noise is not too low. Peak height and width could be based on all peaks, not just those determined to be singleton peaks. Property maps of non-singleton peaks might also be determined and used in rules; e.g., property maps for peaks containing exactly two bases.

Individual peak locations known. TRUE if and only if variable PKS is not empty.

Local average resolution. For a given migration time, look up singleton peak width and spacing in the singleton-peak property maps. Local average resolution is 0.5888*spacing/width.

Make initial base-calls. Assign each previously determined peak one base if its normalized height exceeds 30% of the maximum amplitude found for that dye channel in a 1000-point time window. The number of base-calls for each peak is recorded in the variable PKS.BASES.

Measure properties of all peaks, use to estimate number of base-calls, N. For each peak P, determine the following properties:

Area=sum of signal in P's channel from lower to upper time boundaries, inclusive.

HH=expected half height for singleton peak for given P's channel & migration time.

W=expected full width at half maximum amplitude for singleton peak at given P's migration time.

$\Delta t$=expected base spacing at P's migration time.

Width=width of P at height HH.

Skyline=number of time points within P's time boundaries for which the amplitude in P's channel, normalized to HH, is greatest among all channels when similarly normalized. (Skyline is the number of time points over which the peak's channel "dominates".)

Nw (base-calls based on width)=1+(Width−W)/$\Delta t$ $N_{min}$=floor(Nw)

Excess width=Nw−$N_{min}$

Excess skyline=Skyline/$\Delta t$−$N_{min}$

N (initial number of bases)=$N_{min}$ if excess width <0.5 and excess skyline <0.6, and ceiling(Nw) otherwise.

The rationale for the formula for Nw is that for a peak containing a single base, Width should be roughly W, and extending to the general case for a peak containing 1+N bases, Width should be approximately W+N×$\Delta t$. The subsequent refinement of N simply assumes that peaks having greater width or skyline are more likely to contain an extra base. In computing N, any multiparameter function may be employed. The parameters may include the previously estimated number of base-calls for the given peak and for neighboring peaks, weighting factors, etc.

$N_{min}$. The minimum number of base-calls that a peak's height, width, and skyline would predict. A parameter determined and recorded whenever peak properties are measured.

No other rule for assigning bases has fired. TRUE if and only if the peak object under consideration is still flagged as active.

Normalized peak skyline, height, or width. Divide the measured property for the peak by the value looked up in the map of the corresponding property expected for singleton peaks.

Number of strong minima in second derivative of signal. Within the lower and upper time limits of the peak, determine the number of minima in the second derivative for the peak's channel whose magnitude is at least one third that of the greatest such magnitude in the region. Determination may include local signal-to-noise estimate, current base-spacing estimate, etc.

Peak-containing region known. TRUE if and only if variable PKS_REGION is not empty.

Peak is unusually wide for only N bases. The property "excess width" is determined whenever peak properties are measured. The unusually-wide criterion is satisfied if this property is more than half the expected width of a singleton peak at the given migration time, as determined from the map of singleton-peak width. It would be possible to have different thresholds for different values of N, or to use uncertainty measures or fuzzy logic to reflect varying degrees of "unusually wide".

Peak area small for N bases. The combined area expected for N singleton peaks of Gaussian shape is computed from H and W, the expected singleton height and width at the peak's location. This area is approximately N×H×W×1.06. The measured peak area is small for N bases if multiplying by the factor N/(N−1) gives a result less than 120% of the expected combined area for N singleton peaks. As given for two previous subsections, peak shape may be arbitrary, and in particular may be the shape estimated at that migration time from the most recent base-calls.

Peak height threshold for one base-call. For the migration time supplied, look up singleton height, H, in the map of expected singleton heights for the peak's dye channel. Divide the observed peak height by H and multiply the result by 0.5.

Peak area threshold for one base-call. For the supplied migration time, look up singleton height, H, and width W, in the singleton peak maps for the peak's dye channel. The threshold is (H*W)/2.

Signal derivatives determined. TRUE if and only if variable Y2 is not empty.

Singleton peak widths are accurate. TRUE if and only if PKBASES (entire set of base-calls) have been updated at least twice. Convergence could also be used rather than a fixed number of iterations.

Subdivide peaks using derivatives. The base assignment rules more often produce correct results if the bases assigned to a particular peak are consecutive bases in the final DNA sequence. To increase the likelihood of this condition, the second derivatives of the dye channel amplitudes are used to identify locations at which a peak in a given channel may contain nonconsecutive bases in the final sequence. Peaks at such locations are split into two separate peaks at a likely location of the intervening base from another channel.

The procedure is executed as follows. For each peak, determine whether the outer edges of the peak contain between them more than one minimum in the peak channel's second derivative. If so, then for each successive pair of such minima, determine whether the pair brackets a strong minimum in the second derivative of another channel. A strong minimum is defined as any minimum where the undifferentiated channel amplitude is at least 50% of the expected value for singleton peaks at that particular migration time. Positions of all minima are precorrected for dye mobility.

For each pair of minima that are found to bracket a strong minimum in another channel, find the location of the maximum in the second derivative original peak's channel occurring between the pair. Split the peak by creating two daughter peaks, one extending from the start of the original peak to the location of this maximum, and the other extending from the following time point to the end of original peak. For the daughter peaks, determine the additional peak properties established when peaks are initially detected (location, height, etc.). Other features than the derivatives might be used to subdivide peaks; for example, the positions of peak maxima (rather than minima in second derivative) in other channels.

Having describe preferred embodiments of the present invention, it will now become apparent to those of ordinary skill in the art that other embodiment and variations of the presently disclosed embodiment incorporating these concepts may be implemented without departing from the inventive concepts herein disclosed. Accordingly, the invention should not be viewed as limited to the described embodiments but rather should be limited solely by the spirit and scope of the appended claims.

We claim:

1. A method of analyzing DNA sequencing electropherograms comprising the steps of:
    obtaining a signal produced by a sequence of electrophoretically separated DNA fragments;
    utilizing an expert system including a knowledge base and an inference engine to determine a plurality of base-calls from said signal,
    wherein said inference engine executes at least one rule for measuring properties of a plurality of peaks to estimate a number of base-calls, and
    wherein said rule for measuring properties of a plurality of peaks to estimate a number of base calls comprises the steps of:
        determining a height for a singleton peak;
        determining a full width at half height for said singleton peak;
        determining base spacing; and
        calculating a number of base-calls by subtracting said full width at half height for said singleton peak from a measured width at said half height for a selected one of said plurality of peaks to obtain a first value, dividing said first value by said base spacing to obtain a second value, and adding 1 to said second value.

2. The method of claim 1 wherein said inference engine further executes at least one rule for subdividing a first plurality of peaks.

3. The method of claim 2 wherein said rule for subdividing a first plurality of peaks comprises the steps of:
    determining whether at least one peak in the first plurality of peaks includes local maxima separated by a local minimum wherein the difference between the magnitude of the local minimum and the magnitude of at least one of the local maxima is greater than the magnitude of a noise threshold and if so splitting the peak into a second plurality of peaks.

4. The method of claim 3 wherein said rule for subdividing a first plurality of peaks further comprises the steps of:
    determining the noise threshold by modeling signal and noise using a power spectrum.

5. The method of claim 2 wherein said rule for subdividing a first plurality of peaks comprises the steps of:
    determining whether at least one peak in the first plurality of peaks includes at least one local minimum having a magnitude smaller than a predetermined value and if so splitting the peak into a second plurality of peaks.

6. The method of claim 2 wherein said rule for subdividing a first plurality of peaks comprises the steps of:
    determining whether at least one first peak in the first plurality of peaks overlaps in time respective sides of a second peak having a magnitude greater than a predetermined value, the first peak and the second peak being in different dye channels, and if so splitting the first peak into a second plurality of peaks.

* * * * *